United States Patent
Chase

(10) Patent No.: US 10,750,953 B1
(45) Date of Patent: Aug. 25, 2020

(54) AUTOMATIC FEVER DETECTION SYSTEM AND METHOD

(71) Applicant: Arnold Chase, West Hartford, CT (US)

(72) Inventor: Arnold Chase, West Hartford, CT (US)

(*) Notice: Subject to any disclaimer, the term of this patent is extended or adjusted under 35 U.S.C. 154(b) by 0 days.

(21) Appl. No.: 16/863,043

(22) Filed: Apr. 30, 2020

Related U.S. Application Data

(63) Continuation-in-part of application No. 16/673,295, filed on Nov. 4, 2019, which is a continuation-in-part of application No. 16/354,833, filed on Mar. 15, 2019, now Pat. No. 10,467,903.

(60) Provisional application No. 62/670,209, filed on May 11, 2018.

(51) Int. Cl.
| | |
|---|---|
| *A61B 5/01* | (2006.01) |
| *G01J 5/00* | (2006.01) |
| *B60R 11/00* | (2006.01) |
| *A61B 5/00* | (2006.01) |

(52) U.S. Cl.
CPC .............. *A61B 5/01* (2013.01); *A61B 5/7282* (2013.01); *B60R 11/00* (2013.01); *G01J 5/0003* (2013.01); *G01J 5/0025* (2013.01); *A61B 5/0075* (2013.01); *A61B 5/6893* (2013.01)

(58) Field of Classification Search
CPC ......... A61B 5/01; A61B 5/7282; B60R 11/00; G01J 5/0003; G01J 5/0025
USPC ........................................................ 340/588
See application file for complete search history.

(56) References Cited

U.S. PATENT DOCUMENTS

| | | | |
|---|---|---|---|
| 6,037,860 | A | 3/2000 | Zander et al. |
| 6,151,539 | A | 11/2000 | Bergholz |
| 6,327,522 | B1 | 12/2001 | Kojima et al. |
| 6,759,949 | B2 | 7/2004 | Miyahara |
| 7,567,687 | B2 | 7/2009 | Kudo |
| 8,049,609 | B2 | 11/2011 | Takahashi et al. |
| 8,981,966 | B2 | 3/2015 | Stein et al. |
| 8,988,525 | B2 | 3/2015 | Thompson et al. |
| 9,128,290 | B2 | 9/2015 | Kim |
| 9,230,178 | B2 | 1/2016 | Toyofuku |
| 10,175,112 | B1 | 1/2019 | Kuperman et al. |
| 2005/0084659 | A1 | 4/2005 | Dunkel |
| 2008/0291276 | A1 | 11/2008 | Randler |
| 2008/0297374 | A1 | 12/2008 | Usami |

(Continued)

FOREIGN PATENT DOCUMENTS

| | | |
|---|---|---|
| EP | 0640903 A1 | 3/1995 |
| WO | 2014198551 A1 | 12/2014 |
| WO | 2017184061 A1 | 10/2017 |

OTHER PUBLICATIONS

International Search Report for PCT Application No. PCT/US2019/027594 dated May 21, 2019.

(Continued)

*Primary Examiner* — Kerri L McNally
(74) *Attorney, Agent, or Firm* — McCormick, Paulding & Huber PLLC

(57) ABSTRACT

A passive infra-red automatic fever detection system and method for identifying individuals presenting a thermal profile indicative of an abnormally elevated body temperature, either after an initial thermal reading or after the initial thermal reading and one or more subsequent thermal readings. The system and method may be configured for automatic detection, notification, and alarming of individuals with elevated body temperatures that may be indicative of an infection.

30 Claims, 11 Drawing Sheets

(56) References Cited

U.S. PATENT DOCUMENTS

| | | | |
|---|---|---|---|
| 2010/0005044 A1* | 1/2010 | Bowring | G01S 7/025 |
| | | | 706/20 |
| 2012/0038778 A1 | 2/2012 | Klager et al. | |
| 2012/0229643 A1 | 9/2012 | Chidanand et al. | |
| 2012/0326917 A1* | 12/2012 | Kiehne | B60T 7/22 |
| | | | 342/71 |
| 2013/0138371 A1* | 5/2013 | Kennedy | G01R 21/06 |
| | | | 702/64 |
| 2013/0211720 A1 | 8/2013 | Niemz | |
| 2013/0235202 A1* | 9/2013 | Nagaoka | G06K 9/00805 |
| | | | 348/148 |
| 2015/0019098 A1 | 1/2015 | Schrabler et al. | |
| 2015/0035962 A1 | 2/2015 | Nagaoka et al. | |
| 2015/0123816 A1* | 5/2015 | Breed | G08G 1/096783 |
| | | | 340/905 |
| 2015/0161796 A1 | 6/2015 | Choi et al. | |
| 2016/0152232 A1 | 6/2016 | Takahashi et al. | |
| 2016/0180175 A1* | 6/2016 | Bitton | G06K 9/00771 |
| | | | 348/143 |
| 2017/0004365 A1 | 1/2017 | Ono et al. | |
| 2017/0028811 A1* | 2/2017 | Jayasundera | A61B 5/01 |
| 2017/0197617 A1 | 7/2017 | Penilla et al. | |
| 2017/0219240 A1* | 8/2017 | Cassini | G06F 1/206 |
| 2017/0349173 A1 | 12/2017 | Nishiguchi et al. | |
| 2017/0371336 A1 | 12/2017 | Mei et al. | |
| 2018/0011485 A1 | 1/2018 | Ferren | |
| 2018/0029610 A1 | 2/2018 | McNew | |
| 2018/0134281 A1 | 5/2018 | Newman et al. | |
| 2018/0158335 A1 | 6/2018 | Gee et al. | |
| 2018/0204074 A1 | 7/2018 | Kumano et al. | |
| 2018/0234643 A1 | 8/2018 | Kobayashi | |
| 2018/0236985 A1 | 8/2018 | Kim et al. | |
| 2018/0236986 A1 | 8/2018 | Kim et al. | |
| 2019/0061753 A1 | 2/2019 | Tanaka | |
| 2019/0193787 A1 | 6/2019 | Matsumoto | |
| 2020/0019792 A1 | 1/2020 | Sano et al. | |

OTHER PUBLICATIONS

International Search Report for PCT Application No. PCT/US2019/027589 dated Jun. 21, 2019.

* cited by examiner

AUTOMATIC FEVER DETECTION SYSTEM AND METHOD

CROSS-REFERENCE TO RELATED APPLICATIONS

This application is a continuation-in-part application of U.S. patent application Ser. No. 16/673,295, filed Nov. 4, 2019, which is a continuation-in-part application of U.S. patent application Ser. No. 16/354,833, filed Mar. 15, 2019, which claims the benefit of U.S. Provisional Patent Application No. 62/670,209, filed May 11, 2018, each of which is incorporated herein by reference in its entirety.

TECHNICAL FIELD

The present disclosure generally relates to systems and methods for identifying an individual(s) with elevated temperature that may be indicative of a contagious condition (viral, bacterial or other pathogen) in an individual(s) that may pose potential infection danger to other individuals that may be in proximate distance with an incubating or infected individual(s).

BACKGROUND

Current fever detection methods typically rely on a designated person(s) thermally scanning individuals in a manual sequential manner in an attempt to detect only those individuals that exhibit an elevated body temperature as an indication of possible virus infection. Because this approach is dependent on being carried out by the designated person(s), it is fraught with vulnerabilities such as the designated person(s) being swarmed and overwhelmed by a large crowd, potentially missing the scanning of small children while being focused on their parents, etc. Furthermore, said manual scanning methods only result in a snapshot detection opportunity and may greatly miss an individual already infected but not yet presenting an elevated body temperature.

SUMMARY

The present disclosure provides an Automatic Fever Detection System (AFDS) having a passive infra-red based thermal detection system. The system is configured for automatic passive thermal detection of a thermal signature indicative of an elevated human body temperature. The system provides a superior approach to the detection and identification of individuals exhibiting elevated thermal profiles from among a plurality of individuals even when the individuals exhibiting the elevated thermal profiles are amongst a large, moving crowd of people.

The present disclosure utilizes at least one forward-looking passive infra-red (PIR) image sensor mounted in a fixed position relative to the movement of passing humans.

In operation, the system in accordance with the present disclosure provides an automatic means for instantly (or nearly instantly) detecting specifically-selected and filtered thermal wavelengths that are characteristic of humans that have elevated skin (or body) temperatures above what is expected for a healthy human (typically about 98.6° F.) as they are walking or otherwise moving by or laterally crossing the sensor(s) detection field. Since the body temperature for a healthy human may not be exactly 98.6° F. (e.g. may be 98.4° F.), the system may be set with a pre-defined range for what is considered the body temperature for a healthy human (e.g. 98.1° F. to 98.9° F.), and/or the system may be configured with any other predetermined temperature or range of interest set by an administrator of the system. This information may be used to provide an augmented video and/or warning on a display screen. The video may show the positions of the individual or individuals with and/or without a detected elevated temperature and augment the video by providing graphical images, annotations and/or highlighting to identify individuals with and/or without an elevated temperature. Audible alerts may also be provided, as well as automatic video recording of any individual that triggers an alert condition.

Unlike conventional thermal detection systems, which require one or more designated person(s) or operator(s) to be in close contact with selected individuals having their temperatures measured (which presents a secondary infection danger to said operator(s)), an AFDS in accordance with the present disclosure allows multiple individuals to be scanned at the same time and at a safe distance from the operator. Further, unlike conventional systems that utilize fixed thermal displays that do not provide automatic annotation of specific elevated temperature individuals, the AFDS of the present disclosure does not require an operator to constantly watch a display to identify individuals with elevated temperatures from amongst a moving crowd.

Another feature of the AFDS in accordance with embodiments of the present disclosure provides for the normalization of expected body temperatures in groups of individuals that have been traveling together and have been subjected to similar ambient conditions such as temperature, atmospheric pressures, and humidity as well as similar limits of physical activity (e.g. limited mobility within an aircraft). The AFDS has the capability to continually (or substantially continually) average the body temperatures of a number of arriving individuals to arrive at a mean body temperature for the group, and then look for those individuals that exhibit statistically higher body temperature relative to the normalized group temperature. The normalized temperature figure may also be used to set or adjust the expected mean-normal temperature of the system's thermal acceptance window, as well as set or adjust the system's thermal acceptance window width. In the event the system detects a statistical anomaly such as when a normalized group mean temperature rises above a set expected value, the system warns the operator for the potential of an infected group as a whole.

Although the AFDS has been exemplified in a transportation setting, AFDSs according to the present disclosure may also be located and employed in a variety of other settings, such as schools, universities, shopping malls, hospitals, arenas, office buildings, or any other spaces where multiple individuals have close contact with one another and may need to be monitored.

Objects, features and advantages of the present disclosure will become apparent in light of the description of embodiments and features thereof, as enhanced by the accompanying figures.

DETAILED DESCRIPTION

Figure 1:
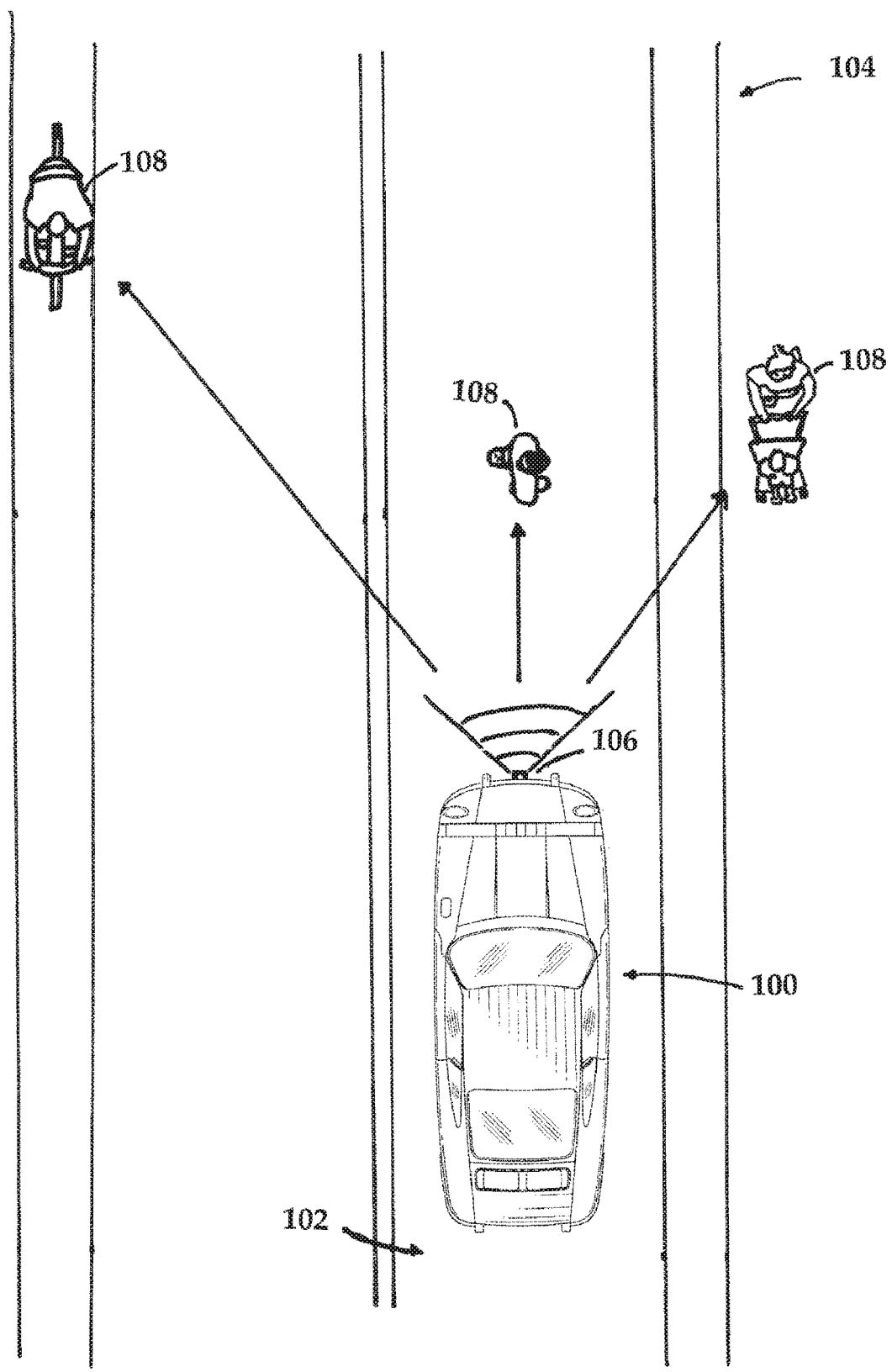
FIG. 1 provides an illustration of a vehicle on a roadway using the system in accordance with the present disclosure to detect direct or lateral human threats to the vehicle.
Figure 2:
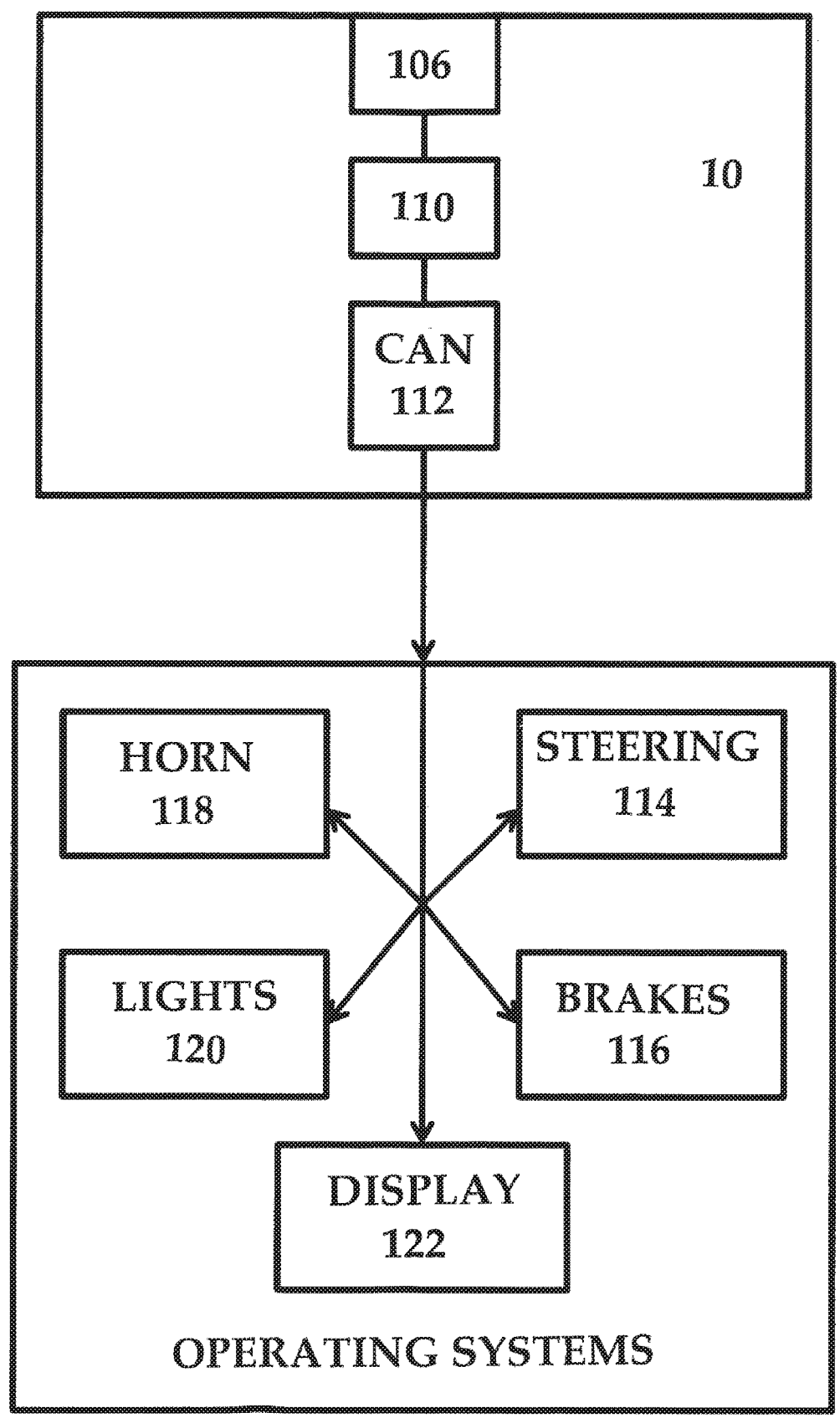
FIG. 2 provides a schematic of a first embodiment of a passive infra-red pedestrian avoidance system in accordance with the present disclosure.

Referring to FIGS. 1-2, a first operational mode of a passive infra-red pedestrian avoidance system in accordance with the present disclosure is illustrated. As illustrated in FIG. 1, a vehicle 100 generally travels within a travel lane 102 on a roadway 104. The system, generally designated by reference numeral 10, comprises at least one forward-looking passive IR image sensor or sensor array, generally designated as reference numeral 106, mounted on the vehicle 100 and directed outwardly in front of the vehicle 100, as the vehicle 100 moves, so that the IR sensor(s) 106 can detect any stationary or moving object(s) 108 containing a human thermal profile in the vehicle's travel lane 102, or in the process of heading towards the vehicle's predicted pathway.

In preferred embodiments of the present disclosure, as generally illustrated in FIG. 1, a single, forward-looking IR sensor 106 is mounted on the vehicle 100, preferably on the front of the vehicle 100, and more preferably centered on the front of the vehicle 100 so that it can detect moving objects 108 relative to both sides of the vehicle 100 on the left and right edges of the roadway 104 ahead of the vehicle 100, as well as any object 108 moving or stationary, already in the vehicle's path. Such a forward-looking IR sensor 106 could dynamically vary the number and area of sensor pixels analyzed depending on a vehicle's forward speed. At higher speeds, an image processor 110 associated with the IR sensor 106 could prioritize the central region of the sensor 106, but as the vehicle's speed decreases, the number and area of pixels analyzed can be increased to effectively widen the sensor's field area(s) of interest. At low speeds, the area of analysis would generally cover a relatively close range in front of the vehicle 100—about 10 to 20 feet in front of the vehicle 100 effectively representing a range from the IR sensor 106 of approximately ±45 degrees from the centerline of the vehicle 100, so as to be able to image the left and right sides of the roadway 104 or travel lane 102 ahead of the moving vehicle 100. Optimally, each IR sensor 106 has a relatively large pixel array in order to effectuate dynamic fields of reference, for example, at least 640×480, from which laterally moving objects can be discerned in accordance with the present disclosure. The number and area of sensor pixels for the thermal acceptance window can also be dynamically varied depending on ambient temperature or weather conditions, roadway conditions, or movement of the object relative to the vehicle.

Figure 5:
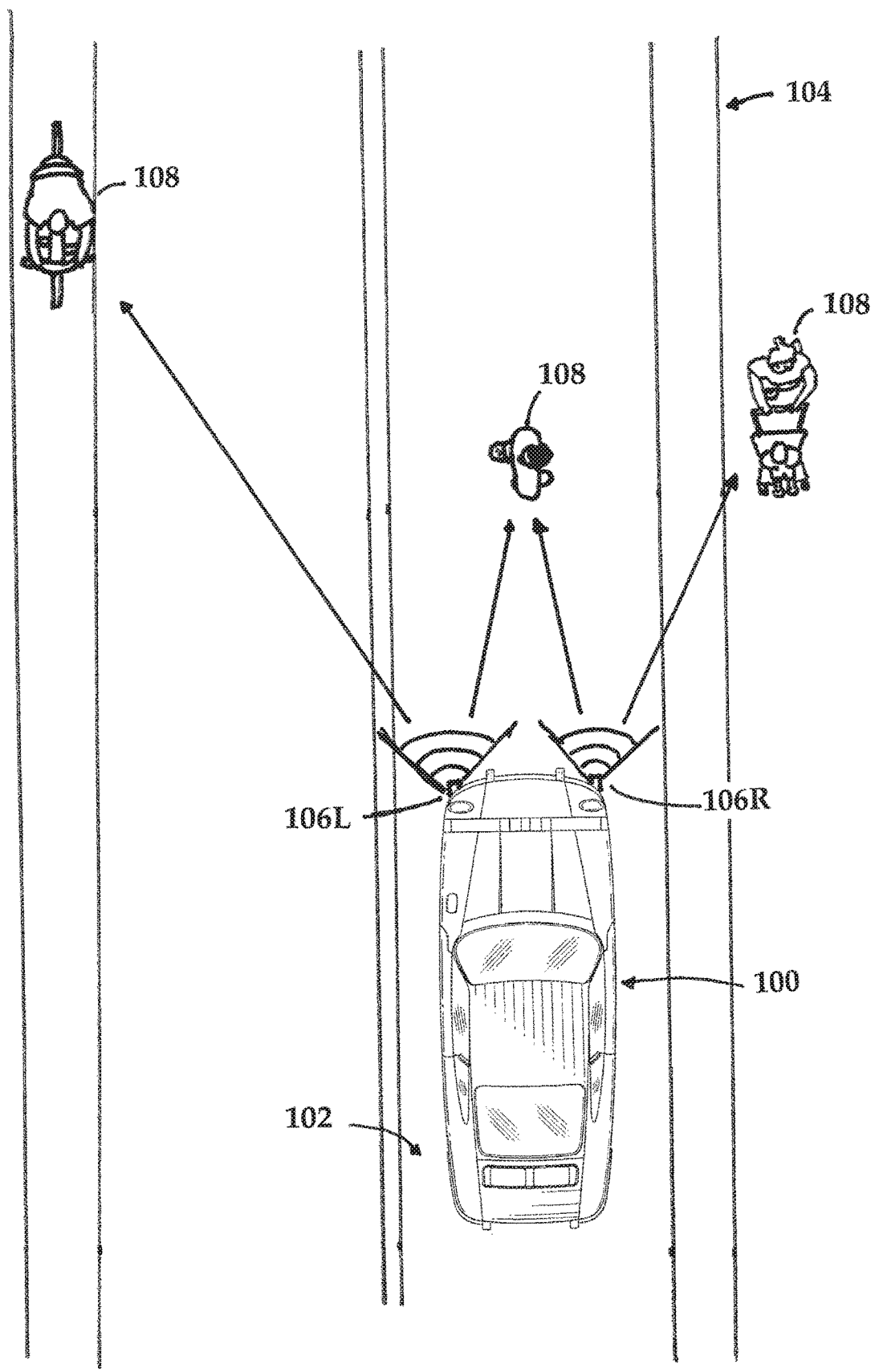
FIG. 5 provides an illustration of a vehicle on a roadway using the system in accordance with an alternate embodiment of the present disclosure to detect lateral threats to the vehicle.
Figure 6:
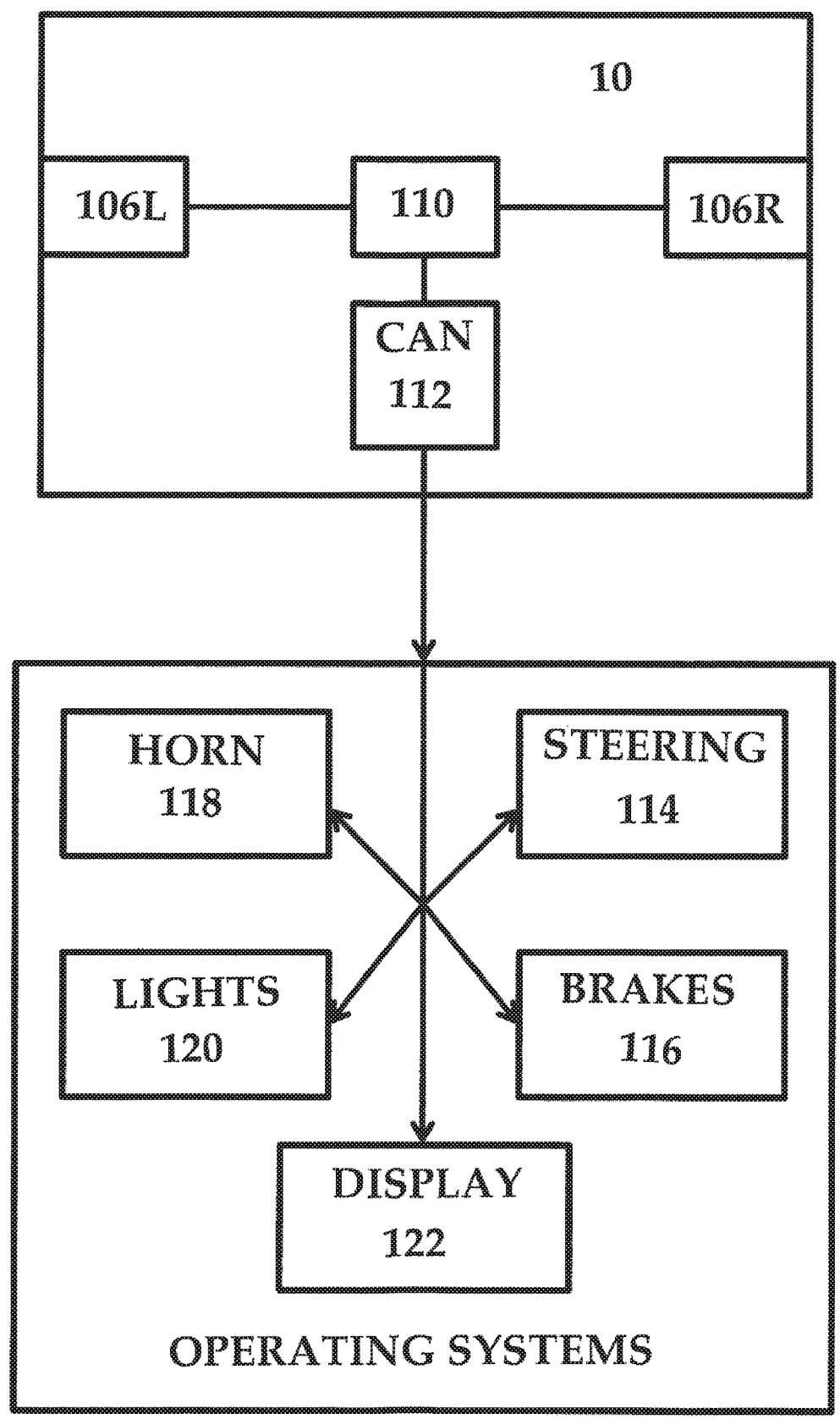
FIG. 6 provides a schematic of a second embodiment of a passive infra-red pedestrian avoidance system in accordance with the present disclosure.

In alternate set-ups of the thermal imaging sensor assembly provided on the vehicle 100, multiple forward-looking IR sensors 106 can be mounted to the vehicle 100, preferably on the front end thereof. Such IR sensors 106 can functionally operate in an independent, over-lapping and/or redundant fashion with each other. In an embodiment of the present disclosure as illustrated in FIGS. 5-6, the vehicle 100 may include a dedicated right-side IR sensor 106R—directed toward the right edge of the roadway/travel lane ahead of the vehicle 100 in a forward-looking manner—and a dedicated left-side IR sensor 106L—directed toward the left edge of the roadway/travel lane ahead of the vehicle 100 in a forward-looking manner. In such an embodiment, the sensors 106R and 106L may be positioned on the front end of the vehicle 100, or alternately, on the lateral sides of the vehicle 100, but directed forwardly from the vehicle 100 so as to detect objects ahead of the moving vehicle 100. More preferably, the sensors 106R and 106L can be directed to be able to detect upcoming objects 108 (e.g., pedestrians and cyclist, as illustrated) on the lateral side of the vehicle 100 in a predictive fashion while also accommodating the movement and speed of the vehicle 100, and further taking into account possible or likely responsive actions the vehicle 100 can take upon detection of a laterally moving threat.

In yet another embodiment, the vehicle 100 can be provided with a combination of front and side IR sensors 106, each still preferably forward-looking, to optimize the detection areas of the system. Again, such IR sensors 106 can functionally operate in an independent, over-lapping and/or redundant fashion with one another. The use of multiple IR sensors 106 can also assist in compensating for variable vehicle speed and ensure that actual and potential threats are quickly identified regardless of the speed of the vehicle 100, the speed of the object 108, the ambient lighting conditions, roadway conditions, or weather conditions.

The discussion of IR sensors and IR sensor array in regards to the present disclosure are intended to be interchangeable, and each embodiment in accordance with the present disclosure covers scenarios using a single sensor as well as an array or set of sensors operating to a collective end of monitoring the lateral sides of the roadway/travel lane ahead of the moving vehicle 100 for potential threats to the vehicle 100, such as pedestrians walking in front of the vehicle 100.

Referring to the schematic illustrated in FIG. 2, the IR sensors 106 are in operative communication with an image processor 110, such as a video processor, tied into the operational system of the vehicle 100, such as via a central CAN Bus unit 112. Preferably, the CAN Bus 112 is in constant communication with various vehicle sensors, such as the IR sensors 106, for analysis and output processing, preferably immediately in real-time, based on the detected data. The image processor 110 filters out any object that is outside a narrow or predefined thermal acceptance window indicative of a normal human thermal profile (e.g., about 98.6° Fahrenheit) before analyzing whether any thermally detected objects are in or are about to enter the roadway 104. The acceptance window can be dynamically widened or narrowed, and/or the thermal center point shifted in accordance with ambient temperature or weather conditions, roadway conditions, lighting conditions, vehicular speed, etc.

In operation, a method for identifying laterally moving dangers for a moving vehicle 100 and adjusting operation of the vehicle 100 accordingly comprises first detecting an object 108, associated with a human thermal signature, on the side of, on a path towards, or already within the roadway 104 along a predicted pathway of the vehicle 100, using thermal imaging (e.g., the IR sensors 106 and the image processor 110). Upon detection and subsequent selection of qualifying objects 108, or potential "threats", the system 10 first determines how many qualified pixels meet the target criteria, as dynamically modified by the vehicle's forward travelling speed. The rate of target pixel change, relative to the vehicle's forward travelling speed, determines how close the vehicle 100 is to a potential object 108. The system 10 then determines if the object 108 is already in the roadway travel lane(s) 102, or moving in a direction toward the roadway travel lane(s) 102, and at what speed, and assesses the need for responsive action in the vehicle's operation.

While the system 10 normally tracks movement of an object 108 relative to the vehicle 100 that has already met the human thermal characteristics, the image processor 110 is also capable of operating in an alternate mode whereby if the qualified object 108 is not moving relative to the vehicle 100, but the vehicle 100 is heading directly toward a stationary qualified object 108, the image processor 110 will count the number of contiguous pixels in a grouping that have met the human thermal profile criteria ("qualified pixels") and consider that increasing numbers of qualified pixels as movement towards a qualified object 108. The numeric threshold of said qualified pixels that are needed to trigger any responsive action(s) may be dynamically changed by the image processor 110 in response to the vehicle's speed and/or the location of the qualified pixels on the sensor array.

If responsive action is identified as being needed, the system 10 triggers such responsive action in the vehicle's operation, such as by providing adjustment input to the vehicle's steering system 114; activating the vehicle's braking system 116; sounding an audible alert 118 associated with the vehicle 100, such as activating the vehicle's horn; and/or activating a visual alert 120 associated with the vehicle 100, such as flashing the vehicle's headlights. For manually driven vehicles 100, additional interior audible alerts, haptic feedback, and/or alerts displayed in front of the driver on the windshield could also be provided.

The step of determining if the human thermal signature is moving in a direction potentially converging with the vehicle 100, for example, with the vehicle's predicted pathway based on direction and speed of the vehicle 100, can involve first, determining if the human thermal signature is moving or stationary upon initial detection thereof; then, determining, if moving, whether the direction of the human thermal signature is generally perpendicular to the roadway 104; and then, determining if the movement is toward the roadway travel lane 102. The step of assessing whether there is a need for responsive action includes determining the speed and direction of movement of the target 108 and/or by determining if the target 108 is within close range of, or already in, the vehicle's predicted pathway. For example, the system 10 can note an increasing number of contiguous qualified thermal pixels reaching a numerical threshold, indicating a proximity reactive threshold. In this regard, other factors can be analyzed, such as ambient temperature, weather conditions, road conditions, vehicle speed, and the like, to modify the reactive algorithm threshold, as described in more detail below.

While generally described herein for use in connection with autonomous—or driverless—vehicles, the system 10 of the present disclosure can also be used in driven vehicles, either having a quasi-autonomous mode or as a back-up redundancy to the human operator. For example, the detected human thermal signature information and suggested corrective action may be provided, for instance, as a "heads up" or overlaid display outline 122 on a driven vehicle 100, or as a data input to the navigation and automatic braking systems 114 and 116, respectively, of the vehicle 100. The driver may be able to adjust the vehicle's position and speed manually, or in the alternative, the vehicle 100 may automatically adjust the vehicle's position, speed, and braking based on such continuous monitoring of any laterally moving threats to the vehicle's operation. If the system 10 detects reactive driver input(s), it can then focus on warning the detected target(s) through the audible and visual signaling systems 118 and 120, respectively, while a driver is focusing on the overall vehicle control.

As noted, the image processor 110 can also be used to detect the presence of human thermal profiles on the side of the roadway 104, and more importantly, when such humans traverse onto the roadway 104 itself. More preferably, the image processor 110 using the system 10 in accordance with the present disclosure, can not only detect the presence of a target object 108 on the side of the roadway/travel lane using thermal imaging, but also determine if the object 108 is moving, in what direction, and at what speed, and adjust operation of the vehicle 100 accordingly. In determining if responsive actions are needed for safe operation of the vehicle 100, as well as what responsive actions are available, the system 10 can predict if a detected human thermal signature is likely to be struck by the vehicle 100 by also taking into account the speed and location of the vehicle 100 relative to the detected human thermal signature; the location of the vehicle 100 on the roadway 104 (e.g., outer lane or inner lane on a multi-lane roadway); the location of the vehicle 100 within a particular travel lane 102; and ambient weather conditions that would potentially impact reaction times for the system and the level of braking force, mindful of distances required to react to a situation properly.

Figure 3:
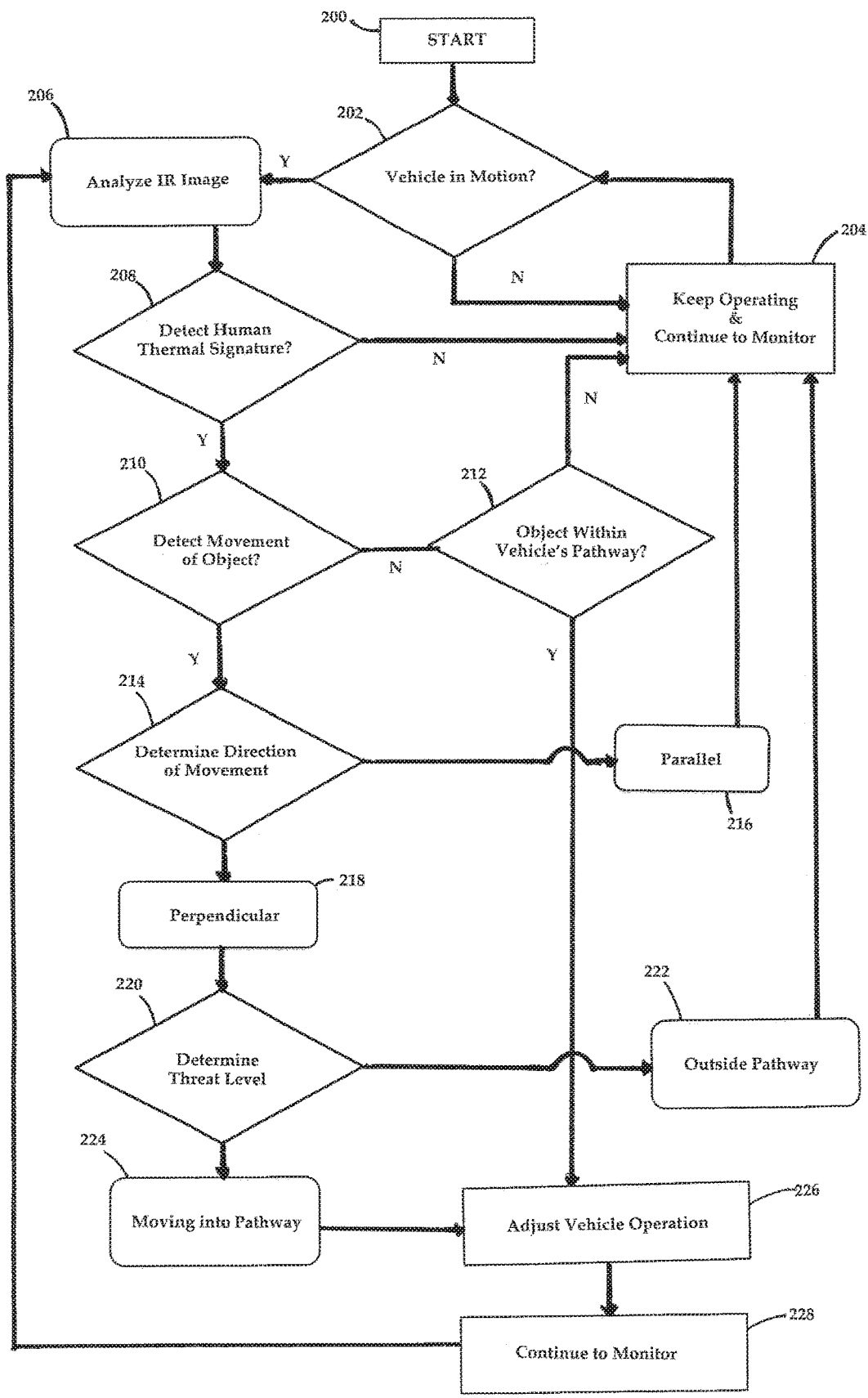
FIG. 3 provides a flow chart generally illustrating an embodiment of a lateral threat detection method in accordance with the present disclosure.

In accordance with the present disclosure, a simultaneous analysis mode, as illustrated in FIG. 3, is available for an autonomous vehicle 100. In operation, the system 10 uses a proprietary algorithm to initially detect the location of objects 108 possessing a human thermal signature (e.g., pedestrians, bystanders, bikers, wheelchairs with human occupants), namely, objects exhibiting a thermal signature that is plus/minus the "nominal" human body temperature of 98.6° Fahrenheit. The algorithm then determines if the detected human thermal signature in said thermal range is already located in, or is moving within, or towards the vehicle's travel area (which would be indicative of a pedestrian or biker), or is maintaining travel in a safe manner within designated bicycle lanes, or at the side of the road for instance. If both the temperature and conflicting movement criteria are simultaneously met, then a logic circuit output will automatically trigger a responsive action in an autonomous vehicle 100, such as activating a vehicle's braking system 116 and/or biasing the steering control system 114 to redirect the vehicle 100 away from the impinging or potentially impinging object 108. Additionally, upon mode activation, the system 10 may activate the vehicle's horn 118 and lights 120 in a distinctive manner to visually and aurally alert and warn distracted pedestrians (such as those looking down at their mobile devices), visually impaired pedestrians, and children running after an object in the roadway, etc. A further implementation of the system 10 would also transmit a warning signal via Bluetooth, V2P, or other signaling means to area mobile devices that are so equipped to receive such safety signals.

In operation, the image processor 110 is specifically looking for and determining whether there is either perpendicular or diagonal movement of human thermal signatures that are about to and/or are in the process of impinging on the upcoming roadway surface of a moving vehicle 100, or stationary human thermal signatures that are existing within the roadway 104 or travel lane 102, while concurrently ignoring strictly parallel "body temperature" movement such as would be typical of bikers or pedestrians walking or biking with traffic along sidewalks or roadway edges or shoulders. These parallel movement(s), unless already located in, or potentially heading into a travel lane or area of pedestrian/vehicle conflict, would lock-out the image processor's output to the vehicle's steering and braking systems so as to avoid untimely or premature triggering of the braking system 116, or untimely or premature steering adjustments by the steering system 114. Detection of thermal objects outside of human thermal signatures would generally be ignored, as these objects would be flagged by other detection systems, such as LIDAR or proximity sensors, which would trigger an appropriate response from those systems based on criteria other than a human thermal profile.

Referring to FIG. 3, an IR lateral detection process using the system 10 in accordance with the present disclosure is illustrated. In preferred embodiments, the system 10 only turns on and operates when the vehicle 100 is turned on, and even more preferably when the vehicle 100 is moving. At Block 200, the vehicle 100 is turned on and the system 10 is activated, preferably in connection with the vehicle's ignition. At Block 202, the system 10 queries the vehicle's operating systems to determine whether the vehicle 100 is moving or not. If not, then the system 10 continues to query about movement on a loop until there is actual vehicle movement, as represented in Block 204. Once the system 10 is informed that the vehicle 100 is moving, the outputs(s) of the IR sensors 106 and motion algorithms, which are already active and searching for and/or detecting qualified targets 108, are analyzed and allowed at Block 206 to pass along the information to the vehicle's operational systems. As noted above, the vehicle 100 can include a single IR sensor 106 positioned on the front-center of the vehicle 100 for detecting objects 108 ahead that may be approaching the vehicle's path from straight ahead, as well as from both lateral sides of the vehicle 100, or in conjunction with two IR sensors 106R and 106L positioned on respective sides of the vehicle 100 for respectively monitoring both sides of the roadway 104 ahead of the moving vehicle 100 to detect objects 108.

If thermal signatures are detected, then the system 10 further determines at Block 208 if the detected thermal object(s) is characteristic of a human thermal profile by passing through a dynamic qualifying thermal gate that is nominally centered around 98.6° F. If not, then the system 10 ignores the object and continues to search for and qualify other detected thermal signatures, again at Block 204. If the object 108 is, however, within the pre-determined human thermal range, it is then classified as a valid detected human thermal signature, and the system 10 then subsequently determines if said human thermal signature is moving, as indicated at Block 210. If no movement is detected, and the object 108 is outside of the travel lane 102 or the vehicle's pathway (Block 212), then the system 10 continues to monitor this and other human thermal signature targets for changes in their movement status without informing the vehicle 100 to take operative action (Block 204). If no movement is detected, and the object 108 is within the travel lane 102, then the system 10 informs the vehicle 100 to take operative action such as holding its present position or adjusting vehicle operation, as necessary (Block 226). If no movement is detected, and the object 108 is safely adjacent to, or within the edges or shoulder of the travel lane 102, then the system takes no operative action. If movement is subsequently detected, then the system 10 determines the direction of the movement at Block 214—e.g., is the movement of the human thermal signature parallel with the vehicle's present and predicted travel, moving away from the vehicle's travel path, or moving towards the vehicle's predicted travel path? In this regard, the system 10 first determines if the movement is parallel to the vehicle 100 at Block 216 (indicating, for example, a person walking or biking within a dedicated lane on the side of the road). If such movement is parallel, then the system 10 determines that the human thermal signature is not in immediate danger from the travel pathway of the vehicle 100 and returns to monitoring this and other thermal signatures for changes (Block 204). The system 10 keeps tracking movement of the detected human thermal signature(s) (Block 218) to identify if its direction of movement shifts to one that could be considered a threat—e.g., a bicyclist turns into the travel lane 102 to cross the roadway 104—until the object 108 is no longer in the filed of view of the IR sensor 106. If such movement is detected, the system 10 re-assesses the actual threat level (Block 220) and determines if any responsive action is needed, as discussed below.

At this stage, where a human thermal signature has been detected and the system 10 is determining if there is movement of the detected human thermal signature, the system 10 can utilize a dynamic lateral angle acceptance window to prevent any temperature-qualified slow-speed laterally moving objects outside the lateral angle acceptance window from falsely triggering the system 10. That is, the lateral angle acceptance window, in proportionality to the current speed of the vehicle 100 and the speed of the detected human object 108, can eliminate potential threats that are too far away from the side of the roadway 104, or are calculated as to not present a future danger as the vehicle 100 passes by the detected object 108. The angle window is defined from the centerline of the moving vehicle 100—for example, ±45 degrees from the vehicle's centerline. More preferably, the width of the lateral acceptance window can proportionally adjust with the speed of the vehicle 100, such that the window is narrower at lower speeds and wider at higher speeds.

If movement is detected as generally perpendicular to the roadway 104, then at Block 220, the system 10 determines if the movement is moving towards or away from the roadway 104 to assess the threat level to the detected human thermal signature. If the movement is determined to be moving away from the roadway 104, or outside the vehicle's predicted pathway (Block 222), then the threat level is low and is disregarded by the system 10 as it continues to monitor for other qualifying thermal signatures and movements (Block 204). If the movement is determined to be moving towards the roadway 104 in a manner that is calculated to result in a vehicular collision with a pedestrian 108 (Block 224), the system 10 triggers, at Block 226, one or more evasive action responses, including but not limited to activating the vehicle's braking system 116, providing direct input to and activating the vehicle's "Driver Assist" steering system 114, and/or providing visual and audio alerts, such as activating and flashing the vehicle's lights 120 and rhythmically sounding the vehicle's horn 118. Again, if movement is determined to be moving away from the roadway 104 (Block 222), the system 10 can dismiss the detected human thermal signature as being no threat but can keep tracking the movement of the human thermal signature in case the speed and/or direction of movement changes, at which time the threat level can be reassessed.

For more accurate assessment of laterally moving detected human thermal signatures within the lateral acceptance window, an algorithm analyzes the detected human thermal signature's present location, direction of travel, and forward lateral speed relative to the vehicle's present location, travel direction, and forward lateral speed to determine whether the combined travel vectors will result in a collision.

After triggering evasive action responses, as shown in Block 226, the system 10 communicates with the vehicle 100 to return to a normal driving mode and again monitoring for thermal signatures, represented by Block 228, essentially starting the process over again to be on the alert for the next unknown, unexpected, and unpredicted situation.

In operation, as the vehicle speed increases, the braking speed/braking force increases proportionally to be able to properly respond to a threat trigger in an optimized and appropriate manner. As a result, the system 10 dynamically matches the timing of the vehicle's response system and activation thereof by taking into account both the real-time speed of the vehicle and the forward and lateral speed of any detected human thermal signature, as represented in the flow chart illustrated in FIG. 4. For example, if the vehicle 100 is travelling at a high speed, the system 10 triggers responsive actions (such as braking and steering adjustments) more quickly and with faster responsiveness and braking effort than at slower travelling speeds. Similar proactive adjustments to the system's timing of responsive actions and reactive response level thereof can be made in bad weather conditions, such when snow or frozen precipitation are detected by the vehicle's temperature and rain sensors, or in other situations where there is potential for braking/steering impairment. Optimally, these sensor inputs adjust the system's responses to allow for an earlier (and more gentle) initiation of responsive actions so that severe response actions (such as a "panic" immediate stops) on a wet or frozen roadway can be avoided, if possible. That is, if the system 10 is aware of road conditions that would make severe braking responsive actions dangerous, the detection and analysis of potential threats can be automatically modified and/or overridden so that earlier activation and more gradual adjustments to the vehicle's speed and steering are made.

Figure 4:
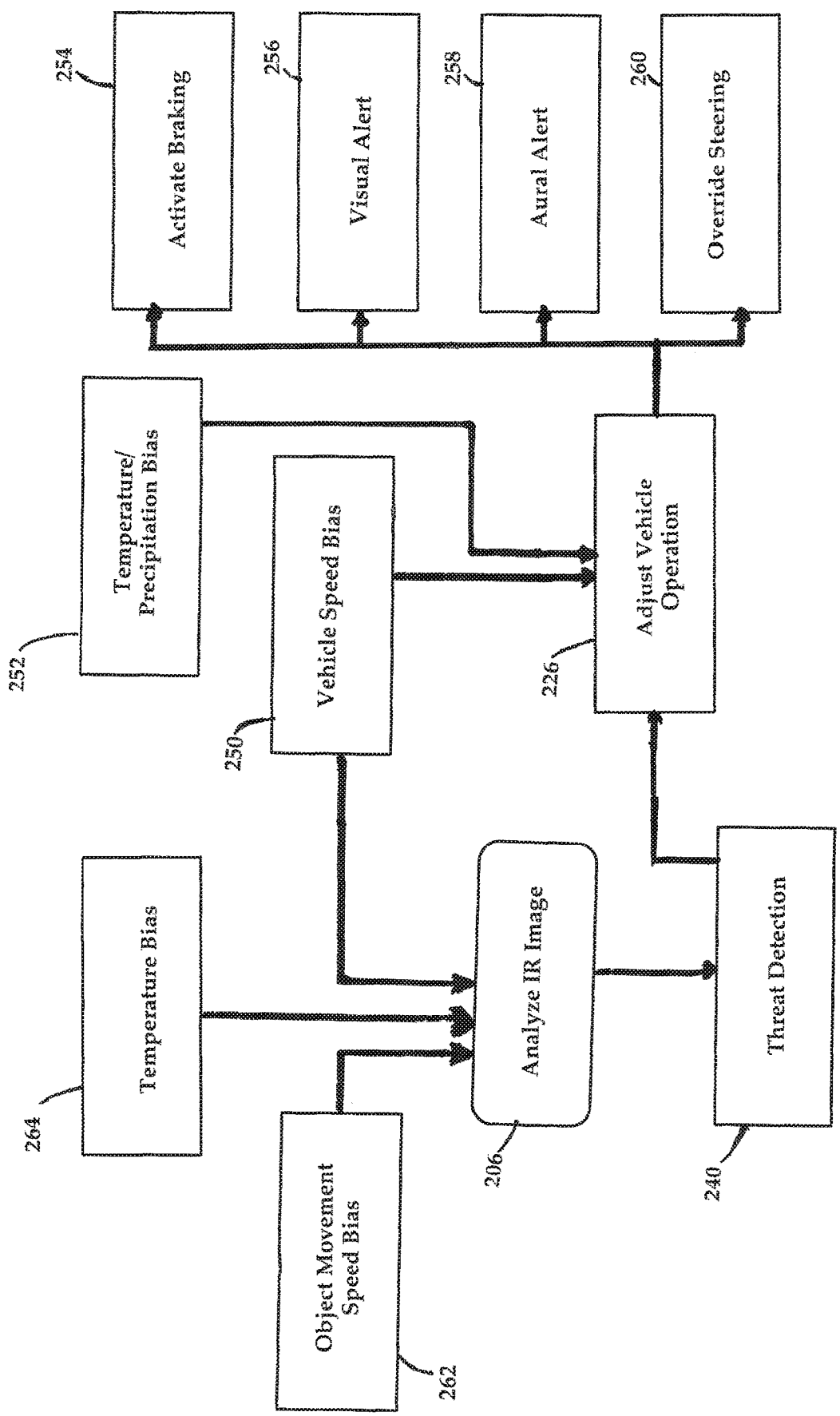
FIG. 4 provides a flow chart generally illustrating another embodiment of a lateral threat detection method in accordance with the present disclosure.

Referring to FIG. 4, a vehicle speed bias (Block 250), as well as a temperature bias (Block 264) and an object movement speed bias (Block 262), are factored into the step of analyzing the outputs(s) of the IR sensors 106 and motion algorithms, which are already active and searching for and/or detecting qualified targets 108 (Block 206). The threat detection process from FIG. 3, and as described above, is represented in FIG. 4 by Block 240. Where a threat is detected and requires responsive action in operation of the vehicle 100, such adjustment of the vehicle's operation (Block 226) factors in the vehicle speed bias (Block 250) as well as a temperature/precipitation bias (Block 252), which may affect the vehicle's immediate adjustment. As further illustrated in FIG. 4, the adjustment of the vehicle's operation can take the form of one or more of a braking activation (Block 254), a visual alert (Block 256), an aural alert (Block 258) and an override and adjustment of the vehicle's steering (Block 260).

The system 10 of the present disclosure is designed to be an adjunct to other sensors and guidance systems, especially during times of challenging ambient conditions, and as such would enhance an autonomous vehicle's guidance system.

As noted, optional IR sensors 106R and 106L that are located on each side of the vehicle 100 with a forward-looking bias would aid in enhancing the detection of potential threats on the side of the roadway 104 ahead of the vehicle 100, as illustrated in FIGS. 5-6. That is, the system 10 could identify an object on the side of the upcoming roadway 104, determine if it is moving toward the roadway 104 and at what speed, and assess whether responsive action would be needed by the time the vehicle 100 approaches the detected human thermal signature's anticipated location.

Unlike many optically-based guidance systems that have diminished effectiveness at night, especially in poorly light sections of the roadway 104, the system 10 of the present disclosure potentially functions even more efficiently at night due to the typically expected greater thermal contrasts between ambient background and detectable targets, especially humans. Optionally, the use of cooling elements for the infra-red imager(s) would further enhance the sensor's temperature discrimination ability.

Figure 7:
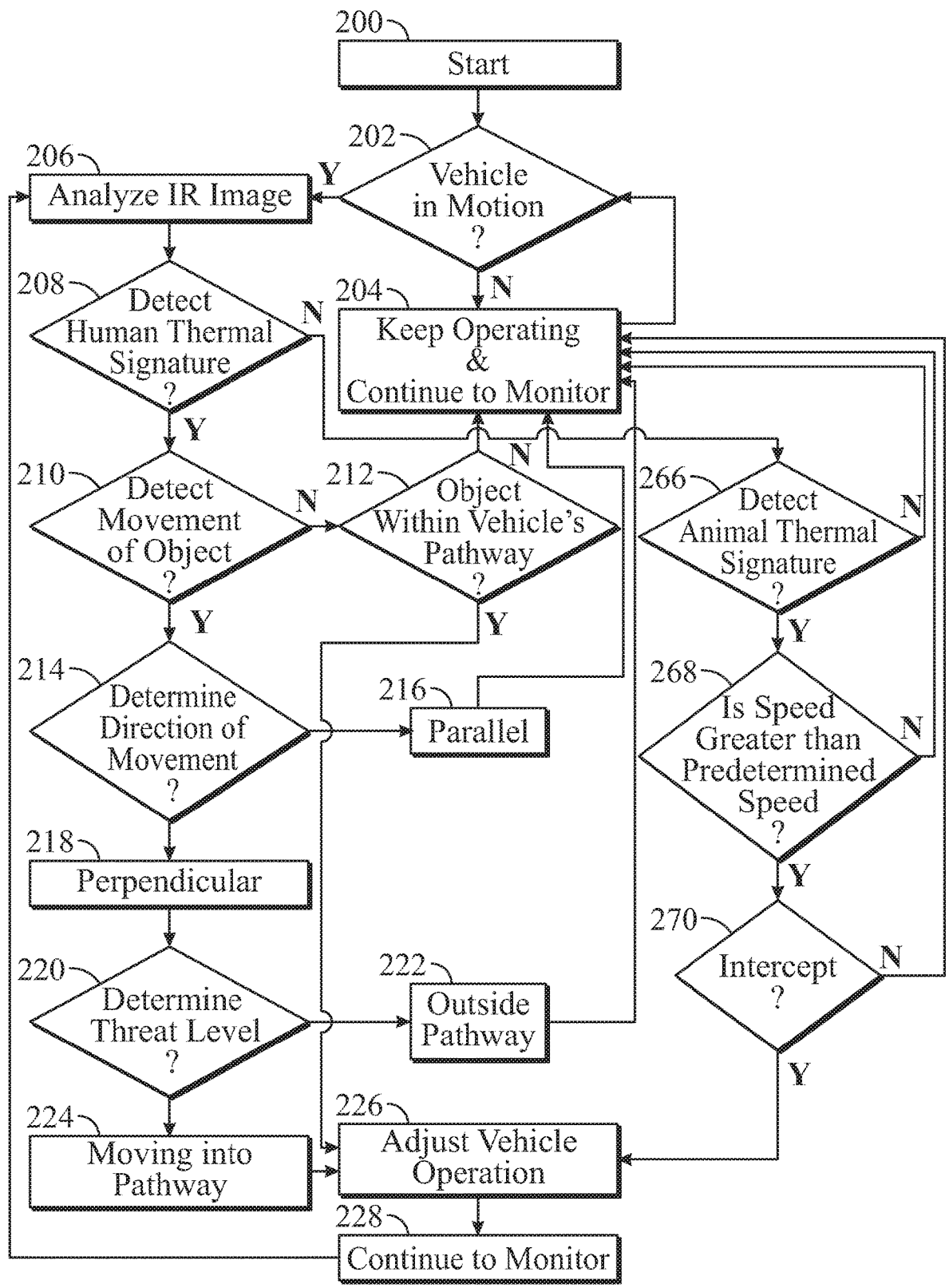
FIG. 7 provides a flow chart generally illustrating an embodiment of a lateral threat detection method in accordance with the present disclosure.

Referring to FIG. 7, an IR lateral detection process using the system 10 in accordance with the present invention is illustrated. The process shown in FIG. 7 is similar to the lateral threat detection process discussed above in connection with FIG. 3 and, therefore, steps 200 through 228, which are the same as those discussed in connection with FIG. 3, will not be described in detail. In the embodiment shown in FIG. 7, if the determination at Block 208 of determining whether a human thermal profile is detected is no, rather than returning to Block 204 and continuing to monitor, the process proceeds to Block 266 for determining whether an animal thermal signature of an animal (non-pedestrian) is detected. If no animal thermal signature is detected at Block 266, the process proceeds to Block 204 for further operating and monitoring of thermal signatures. Alternatively, if an animal thermal signature is detected, the process proceeds to Block 268 to determine if the vehicle 100 is moving greater than a predetermined speed or velocity. If the vehicle 100 is not moving greater than a predetermined speed or velocity, the process proceeds to Block 204 for further operating and monitoring of thermal signatures. If the vehicle 100 is moving greater than the predetermined speed or velocity, the process proceeds to block 270 to determine a potential intercept solution. If the speed and direction (or velocity) of the encroaching animal (e.g. deer) results in a calculated vector of the animal's estimated future position that is in conflict with the vehicle's 100 estimated future position, then the system proceeds to Block 226 to adjust vehicle operation to avoid contact with the animal. For example, the system may immediately apply the vehicle's brakes and/or override steering of the vehicle in an effort to remove a potential intercept between the vehicle and the animal's path. If the distance from the animal, the animal's heading and/or movement speeds of the vehicle 100 and animal indicate that vehicle 100 will "miss" the animal, then the process proceeds to Block 204 for further operating and monitoring of thermal signatures. The vehicle 100 may optionally activate horn and/or lights to alarm the animal in an effort to prevent the animal from entering the vehicle 100 travel path or remaining in the vehicle 100 travel path.

The thermal gate may be centered about a thermal profile of a specific animal, such as deer, moose, bears, cows, pigs, horses, giraffes, camels, etc. In some embodiments, the thermal gate is configured to detect a plurality of different animal thermal signatures. The thermal gate may be a dynamic thermal gate and/or be configured to detect a thermal signature centered approximately around 104° F., for example, in a range of 103° F. to 105° F. or 99° F. to 109° F., which is indicative of a deer. The thermal gate may be configured based on the species, health, season and breeding fluctuations of the deer. As discussed above, the thermal gate center point and thermal window may be dynamically skewed depending on ambient temperature.

Advantageously, in embodiments according to the present disclosure, a passive infra-red pedestrian and animal vehicle avoidance system may be configured to optimize vehicle safety for autonomous, semi-autonomous and/or non-autonomous vehicles. In some embodiments, the system may be additionally configured and/or optimized for animal behavior which is different than pedestrian behavior. For example, the system may be optimized for detection and avoidance of deer, which may move at higher rates of speed than pedestrians, for example, up to 30 MPH. A system 10 equipped vehicle 100 may be traveling at highway speeds (e.g. 55-70 MPH) and be able to detect and initiate preventative measures for avoiding impact and/or mitigating the potential damage of an impact. Collisions with large and heavy animals at speed can be disastrous for a vehicle's occupant(s). Advantageously, such collisions may be avoided or mitigated in accordance with the present disclosure by being configured to detect, warn and/or avoid specific animals.

Figure 8:
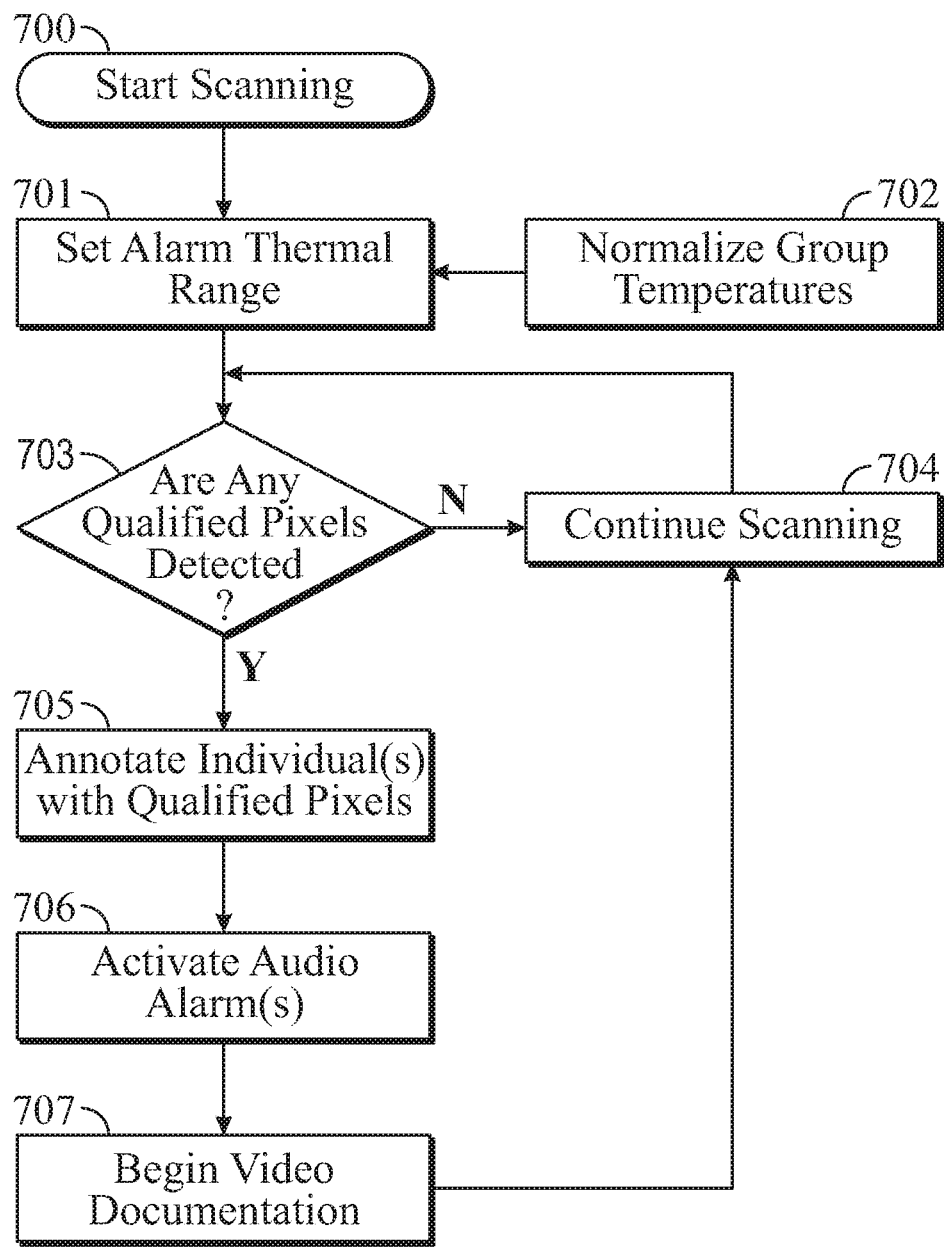
FIG. 8 provides a flow chart generally illustrating an embodiment of a method of operating an Automatic Fever Detection System in accordance with the present disclosure.

Referring to FIG. 8, a flow chart of an operational mode of an automatic fever detection system is shown in accordance with the present disclosure. Operation of the automatic fever detection system begins at block 700 where passive thermal emission detection scanning starts. At block 701, thermal parameters are selected for setting an alarm thermal range. Thermal parameters may include, but are not limited to, a thermal acceptance window center temperature, one or more windows about the thermal acceptance window center temperature, and/or one or more window widths. The scanning process may further optionally be modified at block 702 to normalize a sampled group detected by the scanning, and the normalized group temperature of this sample group may be used as input to set the alarm thermal range at step 701. The processor then searches for any "qualified" pixels representing elevated body temperatures at block 703. A qualified pixel is a pixel that represents a temperature outside the one or more windows set at block 701 and, if applicable, as modified at block 702 for normalization. An elevated temperature is a thermal signature detected through scanning that is above the one or more windows about the thermal acceptance window center temperature. If no qualified pixels are detected or if the number of qualified pixels detected is below a predetermined pixel threshold value, then the process proceeds to block 704 and scanning for qualified pixels continues. In some embodiments, the methods and systems may be configured to be adjustable for a "center" point of each window, a ±temperature range "skew" of each window, and/or a "width" of each window. For example, the center point of a thermal window may have −X/+X degrees of deviation or −Y/+Z degrees of deviation about a center point.

Alternatively, at block 703, if one or more qualified pixels are detected and/or if the number of qualified pixels detected is greater than a predetermined threshold value of qualified pixels, then the process proceeds to block 705 where the individual(s) corresponding to the qualified pixels are annotated on one or more device interfaces, such as, for example, a display device configured to display images or video detected by a visible wavelength camera or other sensor. Then the process proceeds to block 706 and optional audio alarms on or associated with the device interface(s) are activated, such as through a speaker or the like. Audible notifications or indications may be advantageous when the display device is not being actively monitored by an operator (or an administrator or other user). The process then proceeds to block 707 to begin optional image documentation and/or video documentation (or video recording) of the individual(s) identified as having the elevated body temperature. In some embodiments, the image and/or video may always be documented, e.g., recorded, and the portions with the individual(s) detected as having qualified pixels may be copied and sent to a monitoring database, flagged, or time-stamp recorded for future reference, if necessary. For example, an image from the visible wavelength camera may be paired or associated with a thermal record or thermal image from the passive thermal emission detector or sensor for each individual detected by the camera and detector/sensor. Accordingly, an operator or administrator can later view the associated record(s) of an individual and recognize which individual is associated with the thermal signature, e.g. by viewing a still image or video of the individual (with or without annotations) in combination with the thermal record. The image(s) and/or video may be provided to facial recognition software or other identification processing methods and systems, e.g. methods and systems for obtaining individual identification information from a pre-issued identification or entry authorization, including but not limited to passports, driver licenses, boarding pass information, etc., as is discussed in greater detail herein.

In some embodiments the system may automatically alter or allow the thermal window to be manually altered in order to normalize the center and width of the thermal acceptance window based on a plurality of previously detected thermal signatures. For example, the thermal acceptance window may be manually altered in the system by an operator when conditions warrant a different thermal window range and/or width, such as when weather conditions or interior air temperature, pressure, and/or humidity conditions would make it difficult to detect elevated body temperatures. In some embodiments the thermal acceptance window may be skewed to bias the temperature acceptance window exclusively toward the "above normal" direction.

Figure 9:
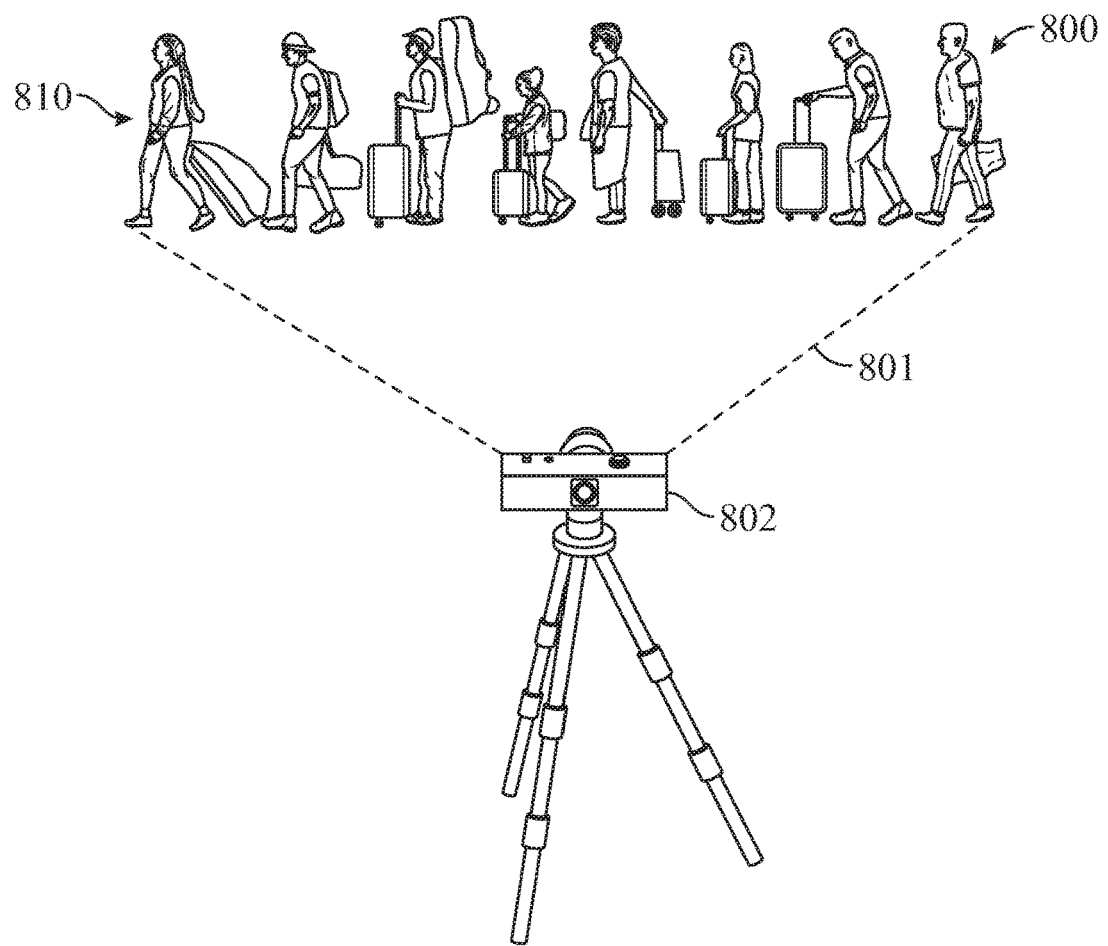
FIG. 9 provides an illustration of an Automatic Fever Detection System in accordance with an embodiment of the present disclosure.

As illustrated in FIG. 9, a group of individuals 800 is shown traveling across the field of vision 801 of the thermal sensor array assembly 802. The system 810 comprises at least one forward-looking passive infra-red (or PIR) thermal image sensor or sensor array 802 mounted at a fixed location and directed toward the individuals 800 as the individuals 800 move past the system 810 in the field of vision 801. This allows the IR sensor(s) 802 to detect if any stationary or moving person(s) 800 are emitting a human thermal profile indicative of an above-normal thermal condition.

Figure 10:
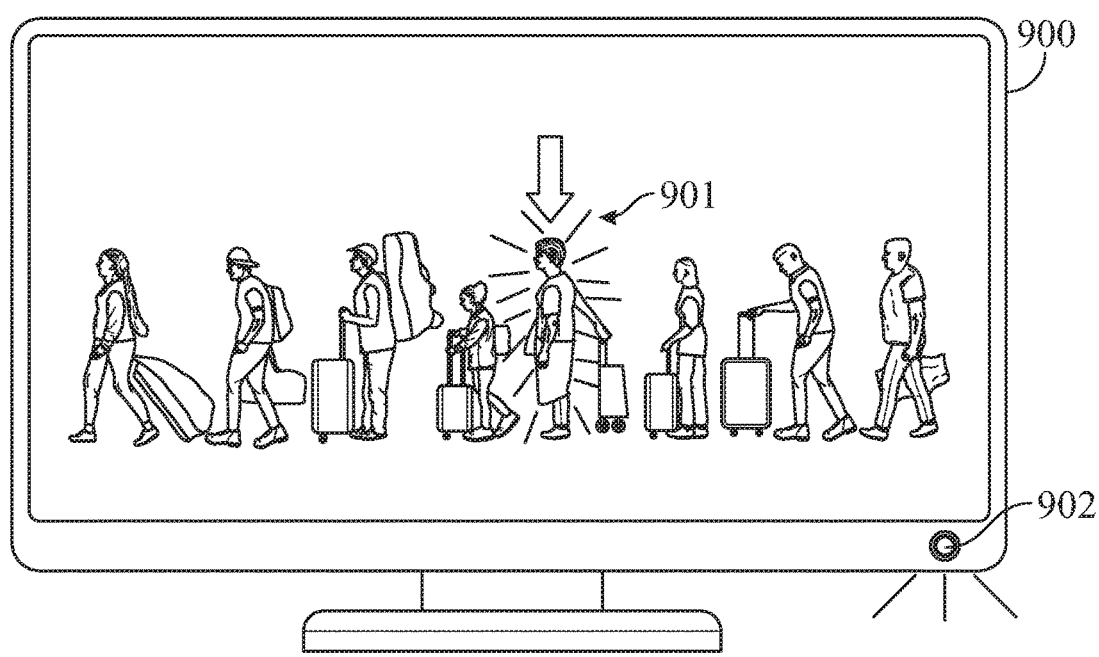
FIG. 10 provides an illustration of an Automatic Fever Detection System in accordance with another embodiment of the present disclosure.

As illustrated in FIG. 10, a display device 900 being operatively connected to the system 810 of FIG. 8 is showing a representative condition where the system 810 has detected and annotated an individual 901 that has been detected as having an abnormally elevated body temperature indicative of an active viral or bacterial infection (or other pathogen). In addition to the visual notification, an audible notification alarm speaker 902 may become active as well, to ensure that a system operator (or administrator or other user) monitoring the system 810 is notified of the individual(s) having the elevated temperature in case the system operator (or administrator or user) is looking away from the display device 900.

While the visual notification for annotation of the individual 901 detected as having the elevated body temperature has been shown in a particular manner in FIG. 10, it should be understood that any visual means of identifying the individual(s) through graphical means is within the scope of the present disclosure. Additionally, while the display device 900 is shown as having the speaker 902 integrated therein, in some embodiments the display device 900 and speaker 902 may be separate components.

Time is often of the essence in not only detecting active cases of deadly viruses or other infections at a point of entry into a country, area, hospital, public venue, or other location, but also the need for fast identification of persons that have been potentially infected by individuals that enter the country with an incubating and non-detectable condition.

As groups of individuals traveling together have been subjected to similar ambient conditions such as, for example, temperature, atmospheric pressures, and humidity as well as similar limits of physical activity (e.g. limited mobility within an aircraft), the AFDS has the capability to continually (or substantially continually) or periodically average the body temperatures of arriving individuals to arrive at a mean body temperature for the group, and then detect those individuals that exhibit body temperature higher than a predetermined amount relative to the group temperature.

If the group temperature rises above a predetermined normalization threshold value, the system may be configured to generate an alert that the group as a whole is detected as having elevated body temperatures, which an operator may determine is an indication that the group as a whole is infected.

In some embodiments, the detection of abnormal temperatures may be used to detect arriving individuals to a country through immigration control.

In some embodiments according to the present disclosure, the detected thermal profiles of individuals are paired with the identification of said individuals in order to generate paired identification/visual image information records. The paired information may be used in real-time applications, but also may be stored for use with subsequent comparisons of future thermal detection sessions of each individual having paired information stored, which may be automatically compared and analyzed. As an example, if a person were thermally scanned on Monday and a subsequent thermal scan was done on Tuesday which showed a statistically significant temperature variation and/or a series of temperature rises, the system would note said variation, generate a report, provide a notification, and/or otherwise flag the individual as exhibiting an abnormal temperature (for that individual) even though the recorded temperatures were outside of commonly used temperature definitions of a human "fever".

One or more AFDSs according to the present disclosure may be located at entrances to office buildings, transportation facilities, hotels, schools, businesses, arenas, prisons, hospitals (either at entrances or in clinician's offices), or other spaces or locations where multiple individuals may have close contact with one another. Conventional facial recognition software may be utilized in conjunction with the AFDS(s) to provide an individual identification basis. In such embodiments, the sensor 802 may be an integrated visible wavelength camera and passive infra-red sensor or, alternatively, the visible wavelength camera may be separate from the sensor 802 and both the camera readings and the passive infra-red sensor 802 readings may be transmitted to a processor of the AFDS. Alternatively or in addition to facial recognition, in locations in which each individual presents a ticket, boarding pass, passport, building pass, ID card, admittance ticket, visitor's pass, or other type of pre-issued identification or entry authorization, the identification information obtained from such item(s) may be automatically or manually passed on to the AFDS, paired with a contemporaneous thermal reading, and then forwarded to a central processing facility of the AFDS. At the central processing facility, the system may then file each individual's record, and if there existed one or more existing records for that individual, the system would add subsequent records to that individual's file, and may then make a comparison to the one or more previous thermal records from that individual in order to determine if there was a thermal difference that could indicate a rising (or falling) temperature that would fit a pre-determined criteria for further analysis, processing, alarm notification, and/or other action.

The AFDS according to the present disclosure includes a processor that is operatively connected to the sensor or integrated camera sensor 802, camera, interface devices 900, one or more databases and central storage and processing facility. The processor may be physically connected to the elements the processor is in operative connection with, or the processor may be physically separate from those elements but operatively connected through one or more wireless and/or wired communication systems. For example, the process may be contained within a computer or display device and wireless connected to integrated camera sensor 802.

The systems, methods and devices according to embodiments of the present disclosure provide an automatic means for instantly (or nearly instantly) detecting individuals with elevated body temperatures via specifically-selected and filtered thermal wavelengths that are characteristic of people with elevated skin (or body) temperatures as they are walking by, laterally crossing, or stationary in front of the sensor(s) and camera(s). The AFDS according to the present disclosure advantageously avoids or mitigates drawbacks associated with thermally scanning individuals via manual means, which is fraught with deficiencies. For example, the manual thermal scan operator has no ability to properly judge an individual's normal or healthy body temperature relative to that temperature which would represent a true elevated body temperature for that individual at least because each individual's normal body temperature can vary relative to that of another individual making such wild (non-contextual) temperature measurements lacking in substantively useful diagnostic value. Additionally, the method of manual spot scanning does not provide for any additional or ongoing continual monitoring of the temperature change of an individual and, therefore, the manual spot scanning may completely miss the detection of infected individuals in the early stage of infection.

The methods and systems according to the present disclosure provide for improved detection of individuals experiencing elevated body temperatures. As discussed herein, in some embodiments, the AFDS may be configured to go beyond the one-time, generalized fever determination and, instead, may look for a true contextual elevated temperature change with that same individual over time, thereby generating individualized thermal assessments for specific individuals over time, regardless of their normal temperature range.

The AFDS may advantageously be configured to simultaneously pair each thermal scan of an individual with corresponding identity information that is self-determined by the AFDS and/or is confirmed or provided by external data sources or databases. Each thermal scan may be recorded and stored, thereby generating a dynamic library of thermal scans performed for each individual scanned by the system, which subsequently allows for either a manual or automatic thermal comparison to be done for the purpose of detecting an elevated body temperature change based on comparing the latest thermal scan with one or more prior scans or based on an average of prior scans. If a thermal scan is the first for that individual to be stored by the system, and thus there is no prior scan for that individual to be compared to, then a generic thermal profile may be temporarily used to determine if that individual is presenting with an elevated body temperature condition.

The identification information for an individual being scanned may be obtained either through onboard commonly used facial recognition software program(s), or by ingesting identification information presented by the individuals themselves as part of an entry process. Such information may be presented to, and then forwarded to, the AFDS by passport readers, identification card or badge readers, entry ticket readers, building pass readers, driver's license Information, or the like.

Once a thermal reading is successfully paired with identification information (or identity information), it is recorded and passed along to a Central Processing Facility(s) for storage and analysis. Said storage may take place on-site, off-site, in a cloud database or computing service, and/or at other locations. In some embodiments, the storage and analysis may occur at a single location or at multiple locations, in some embodiments even simultaneously in multiple locations. The analysis may include one or more processors of the system comparing any prior thermal signatures stored over time from an individual to determine a normal temperature for that individual. Typically, the most recent thermal signature detection would be compared to the most recent prior thermal signature detection, but may also be compared to an average of prior thermal signature detections (or readings). If any successive thermal signature detection results in a variation from the normal reading beyond a predetermined threshold, or a continuing series of increased temperature rises even if still below the strict "fever" definition criteria, the most recent reading is flagged and sent on for further analysis or processing. As each thermal signature detection is recorded, additional information such as time and date of the detection, the location of the thermal reader performing the detection, the identity of the individual, a bus, ship, train or flight number associated with that time period, or the like may also be stored with the thermal signature detection and stored in a database for future reference or use and is appended to the record.

In addition to analyzing any abnormal thermal changes for individuals themselves, the AFDS may also be configured to determine whether there are any clusters of elevated temperatures among numerous individuals, which may be determined and/or sorted by various criteria such as location of the thermal readings, age of the readings, personal data such as flight history, etc. In this way, there can be a near real-time determination of an infectious cluster spread in a highly automated and time-efficient manner.

Figure 11:
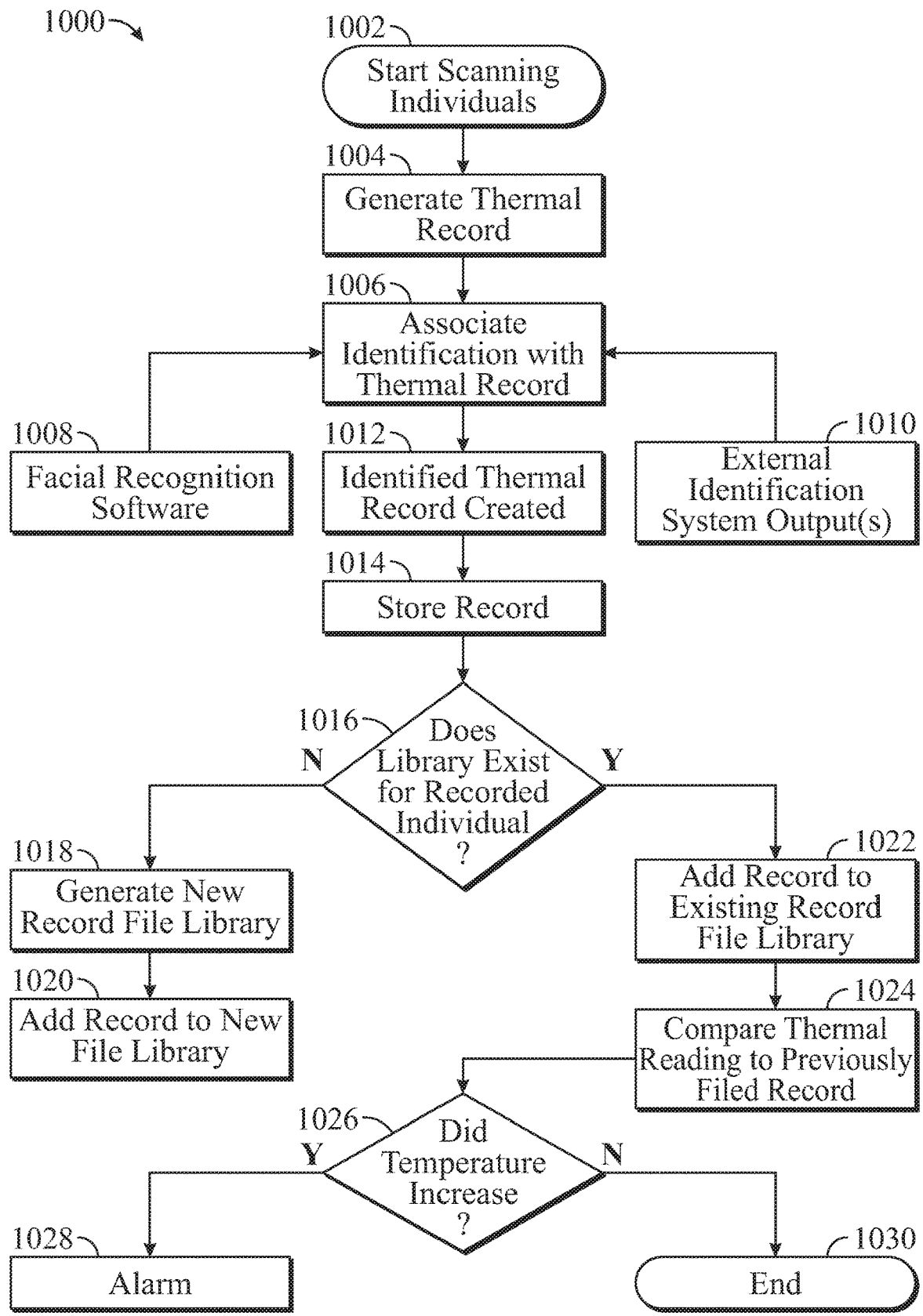
FIG. 11 provides a flow chart generally illustrating an embodiment of a method of operating an Automatic Fever Detection System in accordance with the present disclosure.

Referring to FIG. 11, a flow chart of an operational mode of an automatic fever detection system is shown in accordance with the present disclosure. Operation of the automatic fever detection system begins at block 1002 where passive thermal emission detection scanning with one or more thermal AFDS scanners starts. At block 1004, the system generates a thermal record of one or more individuals. At block 1006, identification information is associated with or added to the thermal record. The identification information is received from facial recognition software processing systems or methods at block 1008 and/or received from external identification system output(s) at block 1010 as discussed above. At block 1012, an identified thermal record is generated for each individual of the one or more individuals. At block 1014, the identified thermal record is stored as discussed above.

The method proceeds to block 1016, where it is determined if the Central Processing Facility(s) contain a library of identified thermal records for each individual. If no library exists for the individual, the method proceeds to block 1018 to generate a new record file library for each individual, and then to block 1020 to add or store the identified thermal record for each individual in their respective new file library. Since there are no prior thermal records to compare the most current thermal record for the individual(s) with no prior thermal records, the system may compare the thermal records of those individuals with a thermal template in order to determine whether the thermal record fits a general indication of an elevated skin or body temperature as discussed above, and an alarm may be activated if applicable. If at block 1016 it is determined that a library exists for the recorded individual, the method proceeds to block 1022 and adds or stores the identified thermal record for each individual in their respective existing record file library. Then the method proceeds to block 1024 to compare the most current identified thermal record generated at block 1012 with one or more previously stored thermal records for the individual. At block 1026, the system determines whether the most current identified thermal record indicates a skin or body temperature increase for the individual. If it is determined that the skin or body temperature did increase, an alarm is activated at block 1028 as discussed above. If it is determined that the skin or body temperature did not increase, the method ends at block 1030, or returns to scanning individuals at block 1002 (or is continuously scanning individuals while performing other steps of the operating method).

Figure 12:
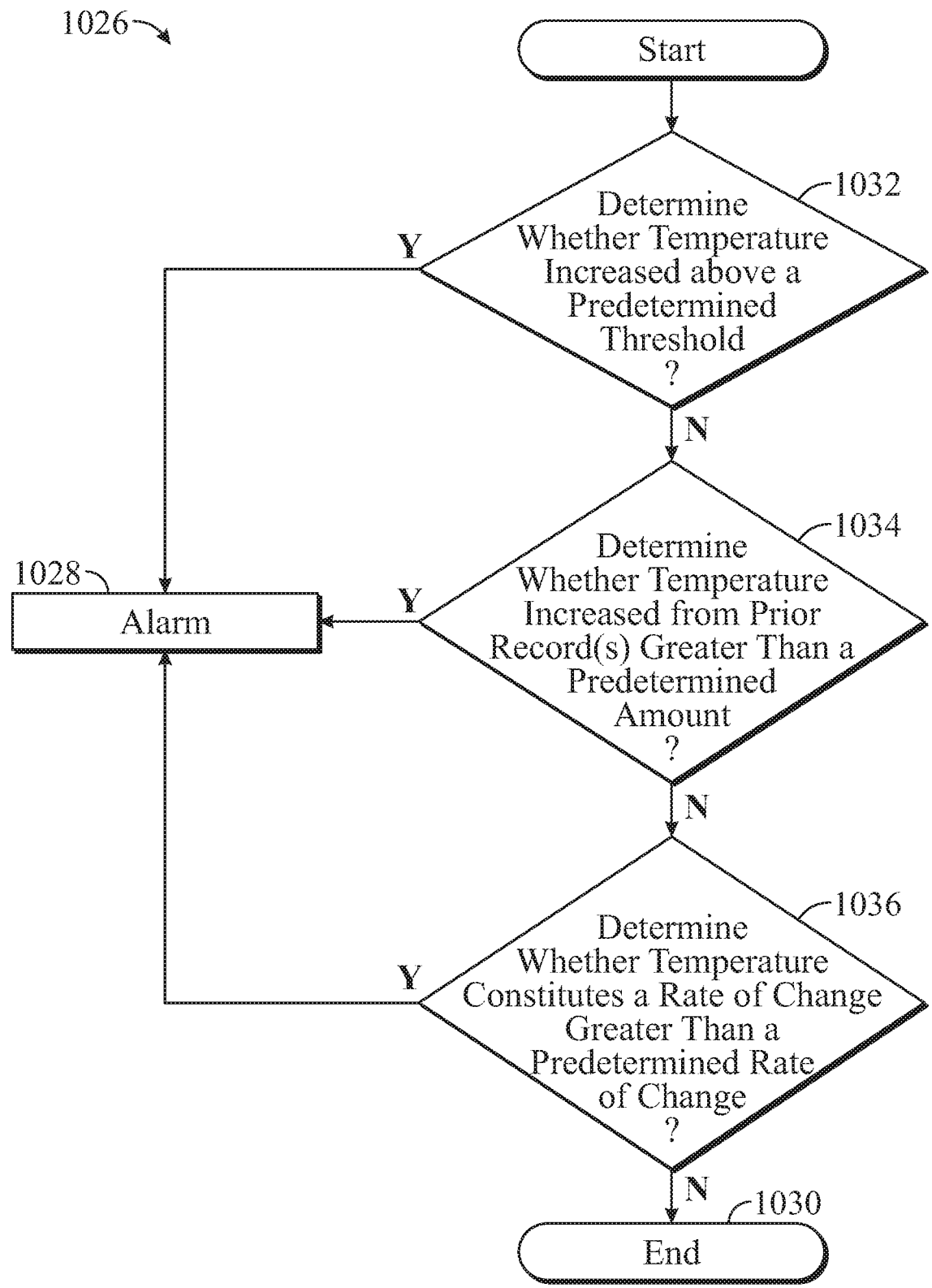
FIG. 12 provides a flow chart generally illustrating a portion of the method shown in FIG. 11 in accordance with the present disclosure.

Referring to FIG. 12, a flow chart of a method that may be implemented for the determination at block 1026 of FIG. 11 is shown in accordance with the present disclosure. The determination 1026 begins at block 1032 where it is determined whether the current thermal reading indicates a temperature increased above a predetermined threshold (e.g. above 100° F.). If it is determined the temperature increased above the predetermined threshold, then the method proceeds to activate an alarm at block 1028. If it is determined that the temperature did not increase above the predetermined threshold, the method proceeds to block 1034 to determine whether the indicated temperature of the individual increased from a temperature indicated by a prior thermal record or average of prior thermal records by an amount greater than a predetermined amount (e.g. an increase in an amount of 2.0° F. or more). If it is determined that the temperature increase was greater than the predetermined amount, the method proceeds to activate the alarm at block 1028. If it is determined that the temperature increase was not greater than a predetermined amount, the method proceeds to block 1036 to determine whether the indicated temperature of the individual constitutes an increase with a rate of change in conjunction with indicated temperature(s) from one or more prior thermal records that is greater than a predetermined rate of change (e.g. if the individual's temperature is increasing at a rate of change of 0.5° F. per day or 0.5° F. per thermal scan). If it is determined that the rate of change of temperature for the individual is greater than the predetermined rate of change, the method proceeds to activate the alarm at block 1028. If it is determined that the rate of change is not greater than the predetermined rate of change, the method ends at block 1030, or returns to scanning individuals at block 1002 as discussed above. The determination at block 1036 may also be configured to proceed to activate the alarm at block 1028 if the rate of change persists for a number of consecutive or successive readings indicating a rising body skin or body temperature greater than a predetermined number of consecutive (successive) readings, even if the rate of change is not greater than the predetermined rate of change, or the absolute temperature readings do not indicate a "formal" definition of a fever in a human. For example, if the individual is recorded as having a rising temperature rate of change three or more consecutive times in a single day, or a rising temperature for three consecutive days. The predetermined number of consecutive (successive) readings is configured to be adjustable by an operator or administrator.

In some embodiments, the determination at block 1026 may comprise all three determinations at blocks 1032, 1034, 1036. In some embodiments, the determination at block 1026 may comprise only one or two of the determinations at blocks 1032, 1034, 1036. It should be readily understood that the order of the determinations at block 1032, 1034, 1036 may be in any order. Advantageously, the determinations at blocks 1034, 1036 may be configured to activate "pre-alarms" when the alarm is activated at block 1028. These alarms would be "pre-alarms" because the individuals with temperatures that result in a "yes" determination at blocks 1034, 1036 do not yet exhibit an absolute temperature that would indicate a fever or elevated skin or body temperature (e.g. at block 1032), but their indicated skin or body temperature records indicate that the changes in their normal temperature warrant further attention or that they will have temperature soon (e.g. as would be recognized as being elevated at the determination of block 1032). Accordingly, individuals with elevated temperatures or individuals who will likely exhibit elevated body temperatures soon may be identified quickly, automatically, and earlier with the methods and systems of the present disclosure than could be accomplished with conventional individual temperature monitoring methods and systems.

It should be readily understood that the Central Processing Facility(s) may be co-located on-side, e.g. in the case of a facility housing a large number of employees, workers, or visitors, or the records may be optionally forwarded in real-time to one or more off-site storage and processing facilities that receives records from numerous locations and other storage and processing facilities.

The system, computers, devices and the like described herein have the necessary electronics, computer processing power, interfaces, memory, hardware, software, firmware, logic/state machines, databases, microprocessors, communication links, displays or other visual or audio interfaces, printing devices, and any other input/output interfaces, to provide the functions or achieve the results described herein.

In addition, a computer readable storage medium may store thereon instructions that when executed by a machine, such as computer, result in the performance according to any of the embodiments described herein.

The foregoing description of embodiments of the present disclosure has been presented for the purpose of illustration and description. It is not intended to be exhaustive or to limit the invention to the form disclosed. Obvious modifications and variations are possible in light of the above disclosure. The embodiments described were chosen to best illustrate the principles of the disclosure and practical applications thereof to enable one of ordinary skill in the art to utilize the invention in various embodiments and with various modifications as suited to the particular use contemplated.

What is claimed is:

1. A method for automatically determining and alerting an operator to the presence of one or more individuals presenting an elevated body temperature, the method comprising:
    detecting one or more thermal signatures using passive thermal emission detection, the one or more thermal signatures being generated by one or more individuals amongst a plurality of individuals, the one or more individuals presenting an elevated body temperature;
    determining if there is a need for a responsive action to the presence of the one or more individuals presenting an elevated body temperature; and
    triggering an alert for an operator if a need for responsive action is determined.

2. The method according to claim 1, wherein the detecting the one or more thermal signatures comprises using a thermal emission sensor array assembly disposed at a fixed position.

3. The method according to claim 1, wherein the step of determining if there is a need for responsive action comprises:
    determining if the one or more thermal signatures is above a predetermined threshold;
    determining if the one or more thermal signatures indicates a temperature increase from a temperature indicated by one or more prior thermal records that is greater than a predetermined amount; and/or
    determining whether the one or more thermal signatures indicates a temperature constituting a rate of change increase in conjunction with one or more temperatures from the one or more prior thermal records that is greater than a predetermined rate of change or that the rate of change persists for a number of consecutive readings greater than a predetermined number of consecutive readings.

4. The method according to claim 1, wherein the detecting the one or more thermal signatures comprises using detected thermal emission data that is passed through a predefined thermal acceptance window correlated to a thermal emission range of a human.

5. The method according to claim 4, wherein the predefined thermal acceptance window is configured to be manually and dynamically altered to compensate for the effect of ambient temperature conditions on the thermal emission range of a human.

6. The method according to claim 4, wherein the predefined thermal acceptance window is configured to be automatically and dynamically altered to normalize the center and width of the thermal acceptance window based on a plurality of previously detected thermal signatures.

7. The method according to claim 6, wherein an abnormal indication notification and alarm is presented to an operator if the predefined thermal acceptance window is dynamically altered beyond a predetermined normalization threshold.

8. The method according to claim 1, wherein the determining a need for responsive action comprises determining if the one or more thermal signatures is above an expected thermal signature reading for a healthy human.

9. The method according to claim 1, wherein the alert comprises:
providing an annotation and/or highlighting to one or more images or to a video on an operationally connected display of each individual exhibiting an elevated body temperature; and/or
activating an audible alert.

10. The method according to claim 1, further comprising recording one or more images of the one or more individuals presenting an elevated body temperature or recording video of the one or more individuals presenting an elevated body temperature.

11. The method according to claim 1, further comprising:
obtaining identification information for each individual of the plurality of individuals;
pairing each individual's identification information with each individual's respective detected thermal signature as paired information; and
storing the paired information at a central storage and processing facility.

12. The method according to claim 11, further comprising:
subsequent detecting one or more subsequent thermal signatures using passive thermal emission detection, the one or more subsequent thermal signatures being generated by one or more individuals amongst a subsequent plurality of individuals, the subsequent plurality of individuals having at least one individual that is part of the plurality of individuals;
subsequent obtaining identification information for each individual of the subsequent plurality of individuals;
comparing the subsequent detections of the one or more thermal signatures with the paired information for each respective individual if the respective individual has paired information stored in the central storage and processing facility; and
determining if the subsequent detection of a thermal signature for an individual of the subsequent plurality of individuals indicates an elevated body temperature in comparison to the paired information for the individual or an average of the detected thermal signatures of the paired information for the individual.

13. The method according to claim 12, further comprising sorting the comparisons of the subsequent detections of the one or more subsequent thermal signatures to dynamically identify clusters of infection amongst individuals, wherein the sorting is based on criteria comprising prior detected locations and/or prior detection times.

14. A system for automatically determining and alerting an operator to the presence of one or more individuals presenting an elevated body temperature, the system comprising:
a thermal sensor array assembly configured to detect one or more thermal signatures using passive thermal emission detection, the one or more thermal signatures generated by one or more individuals amongst a plurality of individuals, the one or more individuals presenting an elevated body temperature;
a processor operatively connected to the thermal sensor array assembly, the processor configured to determine if there is a need for a responsive action to the presence of the one or more individuals presenting an elevated body temperature; and
an interface device operatively connected to the processor;
wherein the processor is configured to trigger the interface device to provide an alert to an operator if a need for responsive action is determined.

15. The system according to claim 14, wherein the thermal emission sensor array assembly is disposed at a fixed position.

16. The system according to claim 15, wherein the thermal emission sensor array assembly comprises a forward-looking thermal sensor aimed at the plurality of individuals.

17. The system according to claim 14, wherein the thermal sensor array assembly is configured to output detected thermal emission data through a predefined thermal acceptance window correlated to a thermal emission range of a human.

18. The system according to claim 17, wherein the predefined thermal acceptance window is configured to be manually and dynamically altered to compensate for the effect of ambient temperature conditions on the thermal emission range of a human.

19. The system according to claim 17, wherein the predefined thermal acceptance window is configured to be automatically and dynamically altered to normalize the center and width of the thermal acceptance window based on a plurality of previously detected thermal signatures.

20. The system according to claim 19, wherein the processor is configured to cause the interface device to generate an abnormal indication notification and alarm for an operator if the predefined thermal acceptance window is dynamically altered beyond a predetermined normalization threshold.

21. The system according to claim 14, wherein processor is configured to determine if the one or more thermal signatures is above an expected thermal signature reading for a healthy human.

22. The system according to claim 14, wherein the wherein the alert comprises:
providing an annotation and/or highlighting to one or more images or to a video on a display of the interface device of each individual exhibiting an elevated body temperature; and/or
activating an audible alert.

23. The system according to claim 14, further comprising a visible wavelength camera operatively connected to the processor, wherein the processor is configured record one or more images generated by the visible wavelength camera of the one or more individuals presenting an elevated body temperature or record video generated by the visible wavelength camera of the one or more individuals presenting an elevated body temperature.

24. The system according to claim 14, wherein the thermal sensor array assembly includes an integrated camera, wherein the processor is configured record one or more images generated by the integrated camera of the one or more individuals presenting an elevated body temperature or record video generated by the integrated camera of the one or more individuals presenting an elevated body temperature.

25. The system according to claim 14,
wherein the processor is configured to obtain identification information for each individual of the plurality of individuals, wherein the processor is configured to pair each individual's identification information with each individual's respective detected thermal signature as paired information; and wherein the processor is configured to store the paired information at a central storage and processing facility.

26. The system according to claim 25, wherein the thermal sensor array assembly is configured to subsequently detect one or more subsequent thermal signatures using passive thermal emission detection, the one or more subsequent thermal signatures being generated by one or more individuals amongst a subsequent plurality of individuals, the subsequent plurality of individuals having at least one individual that is part of the plurality of individuals;

wherein the processor is configured to obtain identification information for each individual of the subsequent plurality of individuals;

wherein the processor is configured to compare the subsequent detections of the one or more thermal signatures with the paired information for each respective individual if the respective individual has paired information stored in the central storage and processing facility; and wherein the processor is configured to determine if the subsequent detection of a thermal signature for an individual indicates an elevated body temperature in comparison to the paired information for the individual or an average of the detected thermal signatures of the paired information for the individual.

27. The system according to claim 26, wherein the processor is configured to sort the comparisons of the subsequent detections of the one or more subsequent thermal signatures to dynamically identify clusters of infection amongst individuals, and wherein the processor is configured to sort the comparisons based on criteria comprising prior detected locations and/or prior detection times.

28. An automatic fever detection system comprising:

a thermal sensor array assembly configured to detect each thermal signature of a plurality of individuals simultaneously;

a visible wavelength camera configured to detect each individual of the plurality of individuals simultaneously;

a display device configured to display images detected by the visible wavelength camera; and a processor operatively connected to the thermal sensor array assembly, the visible wavelength camera and the display device;

wherein the processor is configured to associate each thermal signature detected by the thermal sensor array assembly with each individual detected by the visible wavelength camera;

wherein the processor is configured to determine whether each thermal signature detected by the thermal sensor array assembly is above a predetermined temperature; and wherein the processor is configured to cause the display device to display highlight and/or annotated each individual associated with each thermal signature determined by the processor to be above the predetermined temperature.

29. The fever detection system according to claim 28, further comprising a speaker operatively connected to the processor, and wherein the processor is configured to cause the speaker to emit a sound when the processor determines one or more thermal signatures is above the predetermined temperature.

30. The fever detection system according to claim 28, wherein the processor is configured to determine an identity of each individual of the plurality of individuals, and wherein the processor is configured to store each thermal signature of the plurality of individuals in association with each identity of each individual.

* * * * *